United States Patent [19]

Venturello et al.

[11] Patent Number: 4,550,196

[45] Date of Patent: Oct. 29, 1985

[54] PROCESS FOR THE PREPARATION OF CARBOXYLIC ACIDS STARTING FROM VICINAL WATER-SOLUBLE DIOLS

[75] Inventors: Carlo Venturello; Marco Ricci, both of Novara, Italy

[73] Assignee: Montedison S.p.A., Milan, Italy

[21] Appl. No.: 599,677

[22] Filed: Apr. 12, 1984

[30] Foreign Application Priority Data

Apr. 15, 1983 [IT] Italy ............................. 20605 A/83

[51] Int. Cl.[4] ........................................... C07C 51/285
[52] U.S. Cl. .................................... 562/418; 260/413; 562/493; 562/538
[58] Field of Search ............... 562/493, 528, 538, 418; 260/413 J

[56] References Cited

U.S. PATENT DOCUMENTS 3,855,257  12/1974  Pultinas, Jr. ......................... 562/538

FOREIGN PATENT DOCUMENTS 2262657  9/1975  France .

OTHER PUBLICATIONS

Jacobson et al., *Journal of Organic Chemistry*, vol. 44, No. 6, 1979, pp. 921–924.
Title page and pp. 206–213 of an article by A. S. Perlin in vol. 1 of "Oxidation", edited by Robert L. Augustine, (1969).
C.A. 76 1972, 72034f.
Tetrahedron Letters, 54, 5689–5690, (1968).
C.A. 76, 151485c (1972), abstracting DT 2,106,307 plus copy of the latter.

*Primary Examiner*—Natalie Trousof
*Assistant Examiner*—John Sullivan
*Attorney, Agent, or Firm*—Stevens, Davis, Miller & Mosher

[57] ABSTRACT

This invention relates to a process for preparing monocarboxylic or dicarboxylic acids by means of an oxidative scission of vicinal diols with $H_2O_2$. One starts from vicinal, either terminal or internal, diols soluble in water and, if desired, carrying functional groups that are inert under the reaction conditions. The vicinal diols are reacted in an aqueous solution with $H_2O_2$ at a temperature between 0° and 120° C., and at a pH value between 0.5 and 4, in the presence of a catalytic system consisting of tungstic acid or an alkali metal tungstate, and possibly of phosphoric or arsenic acid or an alkali metal salt thereof.

9 Claims, No Drawings

PROCESS FOR THE PREPARATION OF CARBOXYLIC ACIDS STARTING FROM VICINAL WATER-SOLUBLE DIOLS

DESCRIPTION OF THE INVENTION

The present invention relates to a process for the preparation of carboxylic acids starting from vicinal diols soluble in water. More particularly, said invention relates to a process for the preparation of monocarboxylic and dicarboxylic acids by oxidative scission with $H_2O_2$ of vicinal diols soluble in water.

The monocarboxylic and dicarboxylic acids obtainable by the oxidative scission of vicinal diols soluble in water are chemical products of considerable economic importance. Besides representing useful intermediates for organic syntheses, they find varied industrial applications.

Thus, for instance, adipic acid is used in the synthesis of polyamides, while benzoic acid is a useful intermediate for various syntheses; for instance, its esters are widely used as plasticizers.

The direct selective oxidation of the vicinal diols to carboxylic acids is of considerable interest thanks to the availability of these reactants that may be readily prepared starting from petrochemical products, for instance by hydroxylation of olefines.

The vicinal diols may be oxidized stochiometrically to carboxylic acids by means of a variety of oxidizers, such as $KMnO_4$, cerium (IV) salts, and $K_2Cr_2O_7$.

More conveniently, there may be used catalytic processes based on the use of Caro's acid (with vanadium based catalysts), or peracetic acid (with various catalysts, such as $RuCl_3$ or Co, Mn, Ni, Fe or Pd acetates), or of sodium periodate (with $KMnO_4$ as a catalyst).

However, all the aforesaid processes show serious difficulties of an ecomonic character and/or connected with pollution problems. For instance, the use of sodium periodate as oxidant may, on the one hand, be economically convenient only if it were possible to recover it completely, an operation which, however, is rather difficult. On the other hand, the use of peracetic acid, however, at a relatively high cost, presents the problem of recovery of the acetic acid that is formed as a byproduct of the reaction, and of its use.

It is also known that vicinal diols are oxidized to carboxylic acids by molecular oxygen in the presence of Co(II) salts, for instance the acetate. However, this reaction too presents obvious drawbacks because of the fact that the best yields are achieved when working in expensive solvents (for instance, N,N-dimethylacetamide) and under anhydrous conditions.

On the contrary, the catalytic oxidation of vicinal diols with aqueous $H_2O_2$ is of a doubtless industrial interest thanks to the lower cost of the oxidizer and to the absence of a reduction product to be disposed of. The oxidative scission of vicinal diols with $H_2O_2$ is, however, characterized by poor selectivity.

One object of the present invention is, therefore, that of providing a process for the preparation of monocarboxylic and dicarboxylic acids from vicinal diols soluble in water by making use of aqueous $H_2O_2$, that is, of an oxidizer of limited cost and which does not produce a reduction product that has to be disposed of.

Another object of the present invention is that of providing a process in which there is used a catalytic system at a reasonable cost.

A further object is to provide a process that ensures a high selectivity in respect of yields of the desired acid.

These objects and still others are achieved by the process of this invention for the preparation of monocarboxylic and dicarboxylic acids through the oxidative scission of vicinal diols. This process is characterized in that one starts from vicinal, terminal or internal, diols soluble in water and possible carrying functional groups that are inert under the reaction conditions.

The vicinal diols are made to react in an aqueous solution with $H_2O_2$, at a temperature between 0° and 120° C. and at a pH value between 0.5 and 4, in the presence of a catalytic system consisting of tungstic acid or of an alkali metal tungstate and, possibly, of phosphoric or arsenic acid, or an alkali metal salt thereof.

The reactions are as follows:

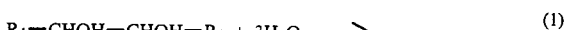

(1)

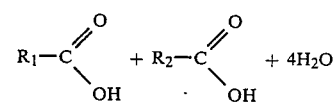

(2)

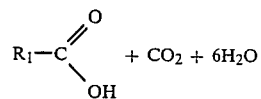

$R_1$ and $R_2$ are hydrocarbon groups (possibly carrying functional groups that are inert under the reaction conditions) such as to allow the solubility in water of the vicinal diols.

As may be seen, reaction (1) relating to the internal vicinal diols, produces two different carboxylic acids:

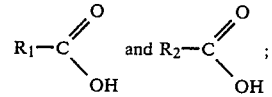

however, if $R_1 = R_2$, there is obtained one acid only.

When the vicinal diol $R_1$—CHOH—$CH_2OH$ is a terminal diol, there is formed

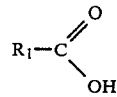

and formic acid which may be oxidized to $CO_2$ in the reaction medium; in such a case, we have reaction (2).

If the internal vicinal diol is a cyclic one, there is formed a dicarboxylic acid.

As already explained, the catalytic system always contains a first component, that is tungstic acid or an alkali metal tungstate and, possibly, a second component chosen from among phosphoric acid or an alkali metal phosphate and arsenic acid or an alkali metal arsenate. Preferably, the catalytic system contains both components; the two-component system, in fact, ensures better yields.

The catalytic system may be formed "in situ" in the reaction medium by introducing into the reactor, together with the vicinal diol, $H_2O_2$ and water, a compound of W and, possibly, of P and As, capable of being transformed in the reaction medium into a tungstate ion and, possibly, into a phosphate or an arsenate ion.

Thus, there may be used as precursors of the first component of the catalytic system, for instance, $WO_2$, $W_2O_5$, $WO_3$, $WS_2$, $WS_3$, $WCl_6$, $WOCl_4$ and $W(CO)_6$.

Analogously, there may be used as precursors of the phosphate ion or arsenate ion, e.g., $P_2O_5$, $As_2O_5$, $PCl_5$, $AsCl_5$, $POCl_3$, $AsOCl_3$, and polyphosphoric acid.

The starting vicinal diols may contain functional groups that are inert under reaction conditions. They may contain, for instance, from 1 to 3 such groups, either equal to or different from each other. Such functional groups also chosen in such a way as to allow the solubility of the vicinal diols in water are, for example, Cl, F and COOH.

Water-soluble vicinal diols that may be conveniently used as starting substances are, for example, 1,2-cyclobutanediol, 1,2-cyclopentanediol, 1,2-cyclohexanediol, 1,2-cycloheptanediol, phenylethanediol, 1,2-propanediol, 1,2-butanediol, 2,3-butanediol, 1,2-pentanediol, 1,2-hexanediol, 3,4-hexanediol, and 3-chloro-1,2-propanediol.

The reaction is conducted under vigorous stirring, after having dissolved in water the catalytic system, the hydrogen peroxide and the vicinal diol and, possibly, after having adjusted the pH of the resulting solution with diluted inorganic acids or bases (e.g., HCl, $H_2SO_4$ or NaOH).

The pH value of the solution in general is between 0.5 and 4, but preferably it is between about 2 and about 3.

The temperature in general is between 0° and 120° C. In practice, the temperature is determined on the basis of the reactivity of the diol and of the stability of the $H_2O_2$. Preferably, one operates between about 60° and about 90° C.

One usually operates at substantially atmospheric pressure.

The duration of the reaction depends on the reactivity of the vicinal diol used. In general, it takes from 5 to 15 hours to complete the reaction.

The catalytic system is used in quantities between 0.01 and 1 mol of W per mol of substrate, but preferably at quantities between 0.02 and 0.15 mols of W per mol of substrate.

When the catalytic system contains both components, these are used in a ratio expressed as mols of W, with respect to the mols of P or As, between 12 and 0.1, but preferably between about 4 and about 0.25.

The vicinal diol and the $H_2O_2$ are essentially used in molar ratios corresponding to the stoichiometry of reactions (1) and (2). However, one preferably uses a moderate excess of $H_2O_2$ (for instance, as excess of 10% with respect to the stoichiometry).

The concentration of the vicinal diol in the reaction mixture varies in general from 1% to 40% by weight, but preferably from about 14% to about 30%.

The concentration of the $H_2O_2$ in the reaction mixture in general varies from 5% to 60% by weight, but preferably from about 15% to about 30% by weight.

At the end of the reaction, the acid or acids are recovered from the reaction medium by recourse to conventional techniques for such recovery.

The following examples are given in order still better to illustrate the inventive idea of this invention.

EXAMPLE 1

Into a 100 ml flask fitted with a reflux condenser and magnetic stirrer there were loaded 0.8 g of $Na_2WO_4.2H_2O$ (about 2.4 mmols), 1.18 ml of $H_3PO_4$ in a concentration of 400 g/lt (about 4.8 mmols), 14.9 ml of $H_2O_2$ in a concentration of 400 g/lt (175.3 mmols), and 6 g of 1,2-cyclohexanediol (cis+trans; 51.7 mmols).

The pH of the resulting solution was then adjusted to the value 2 by the addition of a few drops of a 10% NaOH solution, whereupon the solution was brought up, under vigorous stirring, to 70° C. and was then maintaned at this temperature for 14.5 hours.

The mixture was then allowed to rest overnight in a refrigerator (0°-5° C.).

After filtering the crystals that had formed, through the solution there was first bubbled $SO_2$ until complete destruction of the residual $H_2O_2$, and then $N_2$, in order to remove the excess of $SO_2$.

The solution was then rendered basic with NaOH at a 10% concentration to a pH=8, whereafter it was brought to dryness at 60° C. under vacuum.

The residue was extracted (during 40 minutes) with acetone at boiling temperature, and by subsequent evaporation of the acetonic solution obtained after filtering, there were recovered 60 mg of 1,2-cyclohexanediol.

The solid insoluble in acetone was then dissolved again in the minimum volume of water. The solution was then acidified with a few drops of concentrated HCl and was then allowed to crystallize in a refrigerator. The crystals thus obtained, added to those already previously gathered, were washed with 1,2-dichloroethane, then with icy water (2 ml) and then first dried at the water pump, and then in an oven for two hours at 80° C.

In this way, there were obtained 7.05 g of adipic acid with a 98.9% purity (titer determined by gas chromatography), which correspond to a selectively (calculated on the diol) in adipic acid of 93.3% and to a conversion of the cyclohexanediol equal to 99.0%.

EXAMPLE 2

0.8 g of $Na_2WO_4.2H_2O$ (about 2.4 mmols), 1.18 ml of $H_3PO_4$ at a concentration of 400 g/lt (about 4.8 mmols), 17 ml of $H_2O_2$ at a concentration of 400 g/lt (200 mmols), and 6 g of 1-phenyl-1,2-ethanediol (43.5 mmols) were loaded into a 100 ml flask provided with a reflux condenser and a magnetic stirrer.

The pH value of the resulting solution was then adjusted to 2 by the addition of a few drops of a 10% NaOH solution, whereupon, under vigorous stirring, the solution was brought up to a temperature of 70° C. for a period of 10 hours. Thereupon, after the addition of a 30% NaOH solution until reaching complete solution of the solid that had formed (about 6 ml), the residual $H_2O_2$ was destroyed with $SO_2$.

If necessary, the pH value is brought up again to a slightly alkaline pH with NaOH, whereupon the solution was then brought to dryness under vacuum at 60° C. The residue was extracted (for 40 minutes) with ether under reflux conditions and, by evaporation of the etheric solution obtained after filtering, there were recovered 320 mg of 1-phenyl-1,2-ethanediol. The solid insoluble in ether was, on the contrary, dissolved again in the minimum volume of water and then acidified with 10% HCl.

Benzoic acid precipitated and was filtered, dried at the water pump and dissolved again in ether. By evaporation, after filtering, of the etheric solution, there were obtained 4.07 g of benzoic acid at a 98.8% purity, which corresponds to a selectivity in benzoic acid of 80.1% and to a conversion of the 1-phenyl-1,2-ethanediol equal to 94.7%.

EXAMPLE 3

Into a 50 ml flask provided with a reflux condenser and a magnetic stirrer, there were loaded 0.8 g of $Na_2WO_4.2H_2O$ (about 2.4 mmols), 1.5 g of $Na_2HAsO_4.7H_2O$ (4.8 mmols), 1.5 cc of $H_2O$, 7.5 cc of $H_2O_2$ at a concentration of 400 g/lt (88.2 mmols), and 2.76 g of 1-phenyl-1,2-ethanediol (20 mmols).

With $H_2SO_4$ at a 30% concentration, the resulting solution was adjusted to a pH value of 2 and it was then brought up, under vigorous stirring, to 70° C. for 5 hours.

Thereupon, the procedure was as in Example 2. There were recovered 120 mg of 1-phenyl-1,2-ethanediol and there were obtained 1.62 g of benzoic acid at a 99.3% concentration, which corresponding to a selectivity in benzoic acid of 68.9% and to a conversion of the 1-phenyl-1,2-ethanediol equal to 95.7%.

EXAMPLE 4

Into a 50 ml flask provided with a reflux condenser and a magnetic stirrer, there were loaded 0.8 g of $Na_2WO_4.2H_2O$, finely ground (about 2.4 mmols), 1.2 ml of water, 7.2 ml of hydrogen peroxide in a 400 g/lt concentration (84.7 mmols), and 3 g of 1,2-cyclohexanediol (cis+trans, about 25.9 mmols).

With the addition of HCl, the resulting solution was adjusted to a pH value of 2, after which it was brought up to 70° C., under vigorous stirring, for 7 hours. Thereupon, the procedure was as in Example 1.

There were recovered 40 mg of 1,2-cyclohexanediol, while there were obtained 2.96 g of adipic acid at a 98.4% purity, which corresponds to a selectivity in adipic acid of 78.2% and to a conversion of the cyclohexanediol equal to 98.7%.

What is claimed is:

1. A process for preparing monocarboxylic or dicarboxylic acids by means of an oxidative scission of vicinal diols with $H_2O_2$, characterized in starting from vicinal diols, either terminal or internal, that are soluble in water and possibly carry functional groups that are inert under the reaction conditions; said vicinal diols being made to react, in an aqueous solution, with $H_2O_2$ at a temperature between 0° and 120° C. and at a pH value between 0.5 and 4, in the presence of a catalytic system consisting of tungstic acid or an alkali metal tungstate and possibly of phosphoric or arsenic acid or an alkali metal salt thereof.

2. A process according to claim 1, characterized in that the catalytic system contains both the tungstic acid or an alkali metal tungstate as well as the phosphoric or arsenic acid or one of their alkali metal salts.

3. A process according to claim 1 or 2, characterized in that the catalytic system is prepared in situ in the reaction medium, by introducing into said medium a tungsten compound and, possibly, a phosphorus or arsenic compound, capable of being converted in said medium into a tungstate ion and possibly into a phosphate or arsenate ion.

4. A process according to claim 3, characterized in that the tungsten compound capable of being transformed in the reaction medium into a tungstate ion is chosen from the group consisting of $WO_2$, $W_2O_5$, $WO_3$, $WS_2$, $WS_3$, $WCl_6$, $WOCl_4$ and $W(CO)_6$.

5. A process according to claim 3, characterized in that the phosphorus or arsenic compound capable of being transformed in the reaction medium into a phosphate or arsenate ion is chosen from the group consisting of $P_2O_5$, $As_2O_5$, $PCl_5$, $AsCl_5$, $POCl_3$, $AsOCl_3$ and polyphosphoric acid.

6. A process according to claim 1, characterized in that the pH is between about 2 and about 3.

7. A process according to claim 1, characterized in that the temperature is between about 60° and about 90° C.

8. A process according to claim 1, characterized in that the catalytic system is used in quantities between 0.01 and 1 mol of W per mol of vicinal diol.

9. A process according to claim 1, characterized in that when the catalytic system contains both tungstic acid or an alkali metal tungstate as well as the phosphoric or arsenic acid or one of their alkali metal salts, the molar ratio $$\frac{W}{P \text{ or As}}$$

is between 12 and 0.1.

* * * * *